United States Patent [19]

Rogers et al.

[11] Patent Number: 4,477,329
[45] Date of Patent: Oct. 16, 1984

[54] APPARATUS FOR MAINTAINING PEROXIDE CONCENTRATION

[75] Inventors: Alisa K. Rogers, Granada Hills; Kenneth E. Weber, Pacific Palisades, both of Calif.

[73] Assignee: Lockheed Corporation, Burbank, Calif.

[21] Appl. No.: 410,183

[22] Filed: Aug. 20, 1982

Related U.S. Application Data

[62] Division of Ser. No. 346,168, Feb. 5, 1982.

[51] Int. Cl.³ ............................................. G01N 27/46
[52] U.S. Cl. ................................. 137/93; 204/1 T; 204/435; 148/6.14 R; 423/272
[58] Field of Search .............. 204/1 T, 195 R, 195 P, 204/195 B; 148/6.14 R; 423/272, 273

[56] References Cited

U.S. PATENT DOCUMENTS

| | | | |
|---|---|---|---|
| 3,134,728 | 5/1964 | Goldsmith | 204/195 R |
| 3,367,849 | 2/1968 | Blaedel et al. | 204/1 T |
| 3,539,455 | 11/1970 | Clark | 204/195 P |
| 4,127,448 | 11/1978 | Schick et al. | 204/1 T |

*Primary Examiner*—T. Tung
*Attorney, Agent, or Firm*—Louis L. Dachs

[57] ABSTRACT

A modified alkaline peroxide pre-bond process for the surface treatment of titanium is useful as a practical production process. In this modified process, an exceptionally wide range of allowable peroxide concentration, namely, from 0.001 molar to 0.2 molar (and preferably 0.001 molar to 0.01 molar) may be tolerated and a novel real-time peroxide monitoring and control technique is employed. The process is further improved by means of the use of stabilizers such as precipitated magnesium silicate which greatly increases bath life-time and reduces the overall operating cost of the process. Solution operating conditions have been defined which permit titanium adherends to be processed satisfactorily over a wide range of hydrogen peroxide concentration. In particular, the acceptable temperature range is 125° F.-165° F. (51.7° C.-73.8° C.); the treatment period is 15 to 25 minutes and the hydroxide concentration is 0.3 to 0.9 molar. The preferred values are approximately 145° F. (62.7° C.); 20 minutes, and 0.5 molar, respectively. An electrochemical method has been established utilizing a magnesium electrode (114) which provides a stable potential characteristic that is dependent only on the concentration of the peroxide. The resultant capability to reliably monitor the peroxide concentration in real time in turn permits an automated feed system to be effectively utilized for sustaining the peroxide concentration within the desired limits.

3 Claims, 9 Drawing Figures

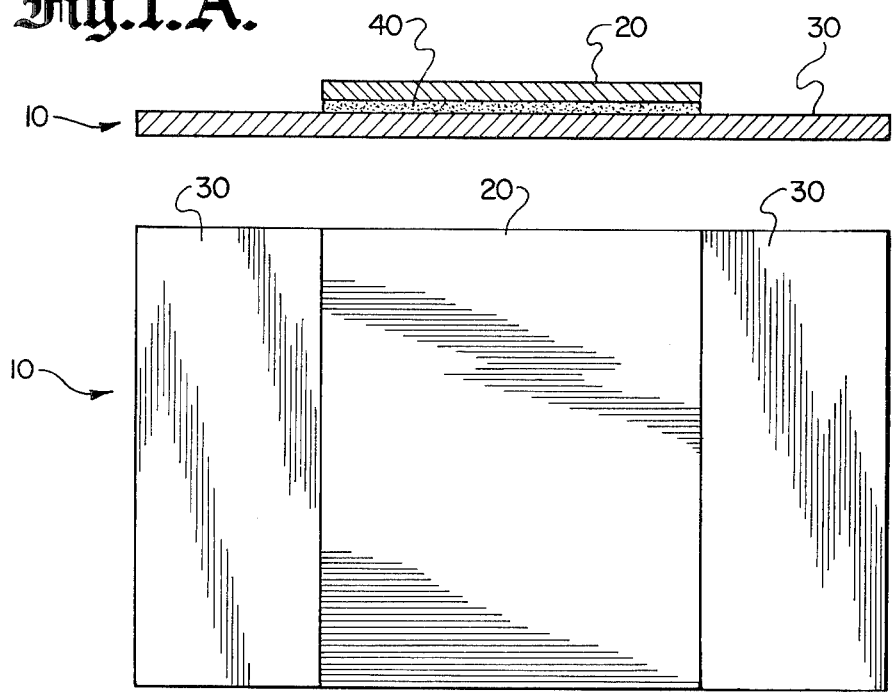
Fig.1.A.
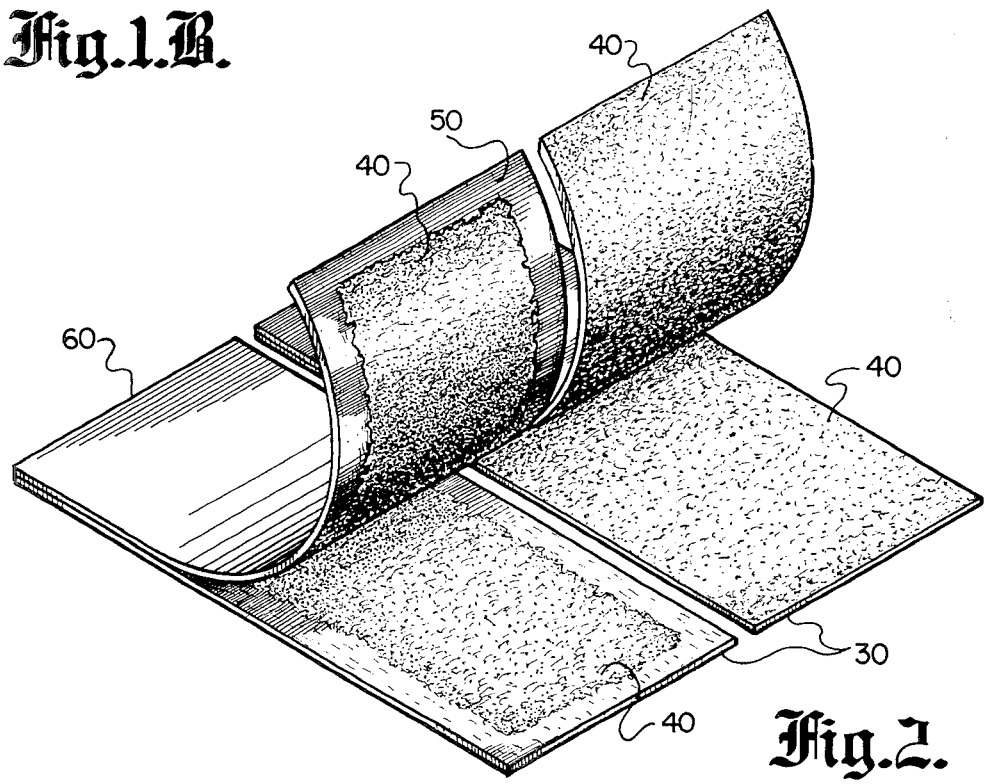
Fig.1.B.
Fig.2.

APPARATUS FOR MAINTAINING PEROXIDE CONCENTRATION

This application is a division of application Ser. No. 346,168, filed Feb. 5, 1982.

TECHNICAL FIELD

The present invention relates generally to the preparation of metallic surfaces in preparation for adhesive bonding and in particular to an improved alkaline peroxide pre-bond surface treatment for titanium that is particularly suitable for large production applications.

BACKGROUND ART

In general, present technology relating to the adhesive bonding of structural metals has the capability of providing bonded joints with satisfactory initial strength properties. The use of bonded titanium structures, however, has been limited because of the susceptibility of the interface between the titanium and the adhesive to environmental degradation. In particular, conventional titanium pre-bond surface treatments such as the phosphate-fluoride process provide an adhesive bond that although possessing adequate initial strength nevertheless lacks resistance to the degrading effects of warm, humid environments.

According to published reports, this environment disbonding problem can be mitigated through the use of an alkaline peroxide pre-bond surface treatment; alkaline peroxide treated adherends consistently have demonstrated superiority in performance over phosphate-fluoride adherends in terms of resistance to disbond in warm, humid environments. It has been speculated that the durability of the alkaline peroxide treated adherends is a result of the rough, porous and relatively stable oxide which is created on the titanium surface.

In addition to providing increased disbond resistance, the alkaline peroxide treatment offers several other advantages. For example, it utilizes a non-polluting treatment solution with relatively low toxicity and presents essentially no waste disposal problem. The treatment solution contains no fluoride which is thought to contribute to the susceptibility of the titanium surface to irreversible morphological changes in the presence of moisture. Moreover, the alkaline peroxide treatment is a one-step process and has the potential of being relatively simple and inexpensive to operate.

Implementation of the alkaline peroxide process into a commercially viable full-scale production process, however, has been hampered by the fact that the hydrogen peroxide component is inherently unstable. This instability characteristic presents quality control and solution maintenance problems uncommon to those of the conventional pre-bond surface treatment processes commonly used in production situations.

Thus, it is an overall objective of the present invention to provide an improved alkaline peroxide prebond surface treatment process that can be readily utilized to provide consistently acceptable performance in a typical factory production line environment in a cost effective manner.

To at least some extent, the decomposition of the hydrogen peroxide is caused by the presence of trace cationic impurities. Certain substances have the potential of absorbing cationic impurities and render them inactive. Avoidance of such impurities is not feasible since the titanium metal being treated contains numerous constituents which will be expected to form cationic species during the surface etching process. Accordingly, it is one specific objective to provide the process with appropriate chemical inhibitors which will react with the various cationic impurities and neutralize their effects.

From published prior art literature, it would appear that concentrations of 0.2 molar $H_2O_2$ and 0.5 molar NaOH are the most suitable for preparing titanium for adhesive bonding; however, in practice, there will be a constant fluctuation of peroxide concentration. Moreover, the rate of decomposition of the peroxide component will be dependent upon the solution's alkalinity. Furthermore, according to at least some published reports "the [alkaline peroxide treated] surface is extremely sensitive to the peroxide bath composition." Thus, it is another specific objective to identify the concentration limits of both the hydrogen peroxide and sodium hydroxide required to obtain a high quality titanium bond. Finally, in order to adapt the process to a production environment, a simple, reliable and safe method for monitoring and maintaining the concentration within such limits is required. Inert platinum or carbon electrodes are unreliable because of contaminants in the solution; dripping mercury electrodes are potentially hazardous. Manual methods are always time consuming and prone to human error. Accordingly, a further objective is to provide a simple, reliable, timely and safe method of monitoring and maintaining the peroxide concentration within the desired limits.

Various aspects of prior art alkaline peroxide solutions and their effects on titanium are discussed in an article by A. Mahoon et al., entitled "A New Highly Durable Titanium Surface Pretreatment for Adhesive Bonding," 10th National Technical Sampe Conf., Vol. 10, Oct. 17, 1978, p. 425 et seq. in an article by J. L. Cotter, entitled "Natural Weathering Behaviour of Adhesive Bonded Titanium Alloy Assemblies", Society of Environmental Engineering Symposium, Apr. 27, 1977; and in a report by M. Natan et al., entitled "Bondability of Ti Adherends II. Humid Environmental Effects," Martin Marietta Final Report MML TR81-42(c), Sept., 1981, which are hereby incorporated in their entirety by reference, as is an article by W. Nicoll et al., entitled "Stability of Dilute Alkaline Solutions of Hydrogen Peroxide", Industrial and Engineering Chemistry, Dec. 1955, p. 2548 et seq.

DISCLOSURE OF THE INVENTION

The alkaline peroxide pre-bond process for the surface treatment of titanium offers excellent initial strength and durability properties for adhesive bonded joints and is potentially attractive for large-scale production applications because of its inherent simplicity and low toxicity; however, the concentration of the hydrogen peroxide component is difficult to maintain with known prior art techniques and excessive quantities of hydrogen peroxide are required as a result of the instability of prior art alkaline peroxide treatment solutions.

In accordance with the teachings of the present invention, the known peroxide process is modified so as to become the basis for a practical production process. In this modified production process, an exceptionally wide range of allowable peroxide concentration may be tolerated and a novel real-time peroxide monitoring and control technique is employed. Experiments indicate that the process produces satisfactory results with peroxide concentrations varying between 0.001 molar and 0.2 molar; however, 0.001 molar to 0.1 molar or even 0.001 molar to 0.01 molar is the preferred range. The process is further improved by means of the use of stabilizers such as precipitated magnesium silicate which greatly increases bath life-time and reduces the overall operating cost of the process.

Solution operating conditions have been defined which permit titanium adherends to be processed satisfactorily over a wide range of hydrogen peroxide concentration. In particular, the acceptable temperature range is 125° F. to 165° F. (51.7° C. to 73.8° C.); the treatment period is 15 to 25 minutes and the hydroxide concentration is 0.3 molar to 0.9 molar. The preferred values are approximately 145° F. (62.7° C.), 20 minutes, and 0.5 molar, respectively.

An electrochemical method has been established utilizing a magnesium electrode which presents a relatively fresh, uncontaminated electrode surface to the solution which possesses stable potential characteristics which depend only on the concentration of the peroxide. The resultant capability to monitor reliably the peroxide concentration in real time in turn permits an automated feed system to be incorporated for sustaining the peroxide concentration within the desired limits for an efficient and reliable production pre-bond treatment process, thereby permitting bonded titanium structures to be commercially fabricated with excellent strength properties and much improved long-term durability characteristics.

BRIEF DESCRIPTION OF THE DRAWINGS

FIG. 1, comprising FIGS. 1a and 1b, illustrates in respective elevational and plan views, the configuration of a typical test specimen;

FIG. 7 is a graph showing the rate of hydrogen peroxide decomposition in solutions containing various inhibitors.

BEST MODE FOR CARRYING OUT THE INVENTION

Figure 3:
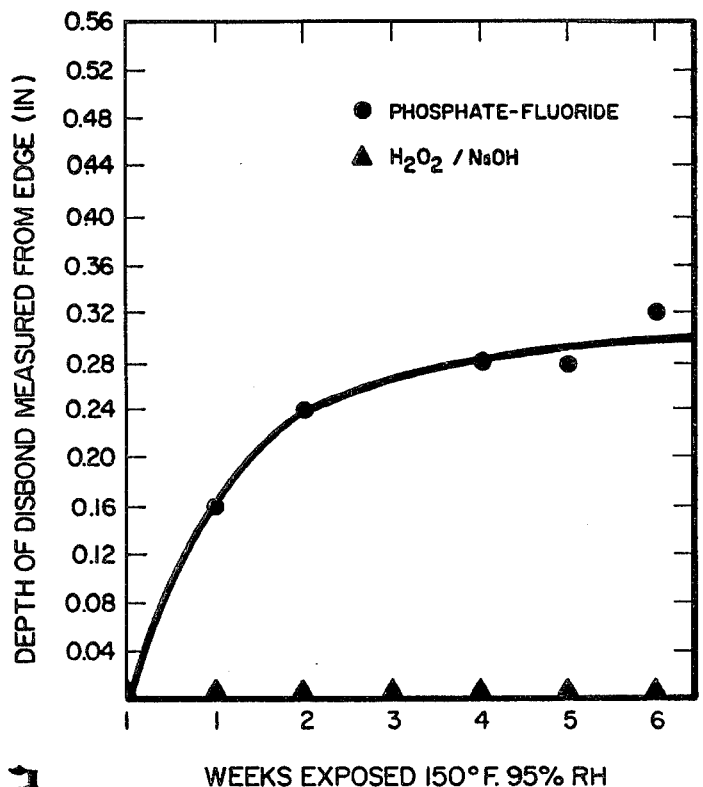
FIG. 3 is a graph comparing the rate of disbond depth in test specimens prepared using different pre-bond processes.

A standardized testing procedure was employed to evaluate the durability characteristics of bonded specimens containing titanium adherends. The configuration of the individual test specimens is shown in elevation and plan views in FIGS. 1a and 1b. Such specimens are intended to be representative of certain types of bonded aircraft joints. Each test specimen (10) comprises a narrower (5"×8"; 127 mm×203 mm), 0.020 inch (0.5 mm) thick unprimered titanium alloy sheet (20) bonded to a wider (9"×8"; 229 mm×203 mm), 0.25 inch (6.3 mm) thick primered aluminum alloy plate (30) by means of an adhesive layer (40). The specimen is placed in a humidity cabinet and exposed to a 150° F. (65.5° C.), 95% relative humidity environment for predetermined periods of time. The titanium adherend portion (20) of the specimen is then hand-peeled from the plate (30) and the adhesively failed disbond area (50) around the edge of each specimen is then measured (see FIG. 2). The disbonded area increases with time of exposure to the high humidity environment; also the rate of disbond increases as the temperature of the high humidity environment is raised.

In the event that a particular adhesive exhibits variability with regard to moisture sensitivity, it may be necessary to dry the durability test specimens in an oven prior to peeling them in order to separate the reversible effects of moisture in the adhesive from the irreversible disbonding phenomenon.

Figure 2:
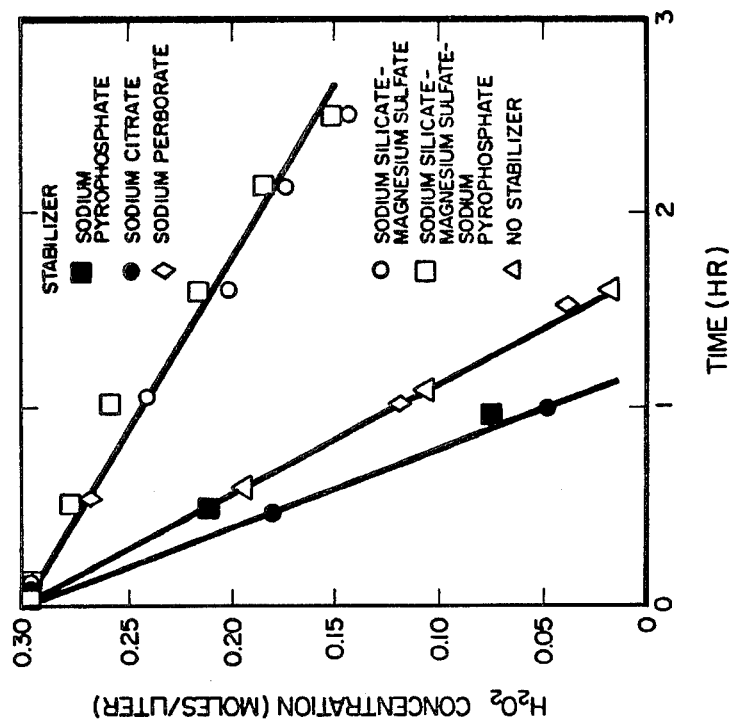
FIG. 2 is an artist's rendering comparing two durability test specimens relating to the effects of humidity exposure on the bonded area.

FIG. 2 provides an artist's rendering of the respective bonded areas of two actual durability test specimens showing the differences in appearance in a peeled specimen due to the effects of humidity exposure on the bonded interface area. One of the adherends (60) shown in FIG. 2 was processed in a phosphate-fluoride bath whereas the other (20) was given the alkaline peroxide pre-bond treatment. The disbonded area (50) of the adherend specimen (60) prepared using the conventional phosphate-fluoride process appears to be completely devoid of adhesive (40). The durability test data, presented graphically in FIG. 3, were obtained from specimens exposed to 150° F. (65.5° C.), 95% relative humidity conditions for extended periods. The data in FIG. 3 show large differences in the rate of disbond penetration corresponding to specimens prepared using the two different processes. FIGS. 2 and 3 thus demonstrate the high resistance to disbond provided by the alkaline peroxide pretreatment method relative to the phosphate-fluoride method. In particular, an analysis of the comparative −67° F. (−55° C.) climbing drum peel data given below in Table I show that the respective initial peel strength provided by both the alkaline peroxide treatment and the phosphate-fluoride methods are essentially the same; however, after 108 hours exposure to 150° F. (65.5° C.), 95% relative humidity, the peel strength for the phosphate-fluoride treated specimens decreased by almost 50% but there was no observed reduction in peel strength associated with the alkaline peroxide treated specimens.

TABLE I

| | | | | |
|---|---|---|---|---|
| Climbing Drum Peel Test Data Comparing the Use of Two Different Pre-bond Treatments. | | | | |
| −67° F. (−55° C.) PEEL VALUE MEASUREMENT | | | | |
| SURFACE TREATMENT | Initial | | Following 108 hrs at 150° F. (65.5° C.), 95% Relative Humidity | |
| | in-lbs/in | cm-kgs/cm | in-lbs/in | cm-kgs/cm |
| Phosphate-Fluoride | 42 | 19 | 23 | 10.5 |
| Alkaline Peroxide | 45 | 20 | 45 | 20 |

Figure 4:
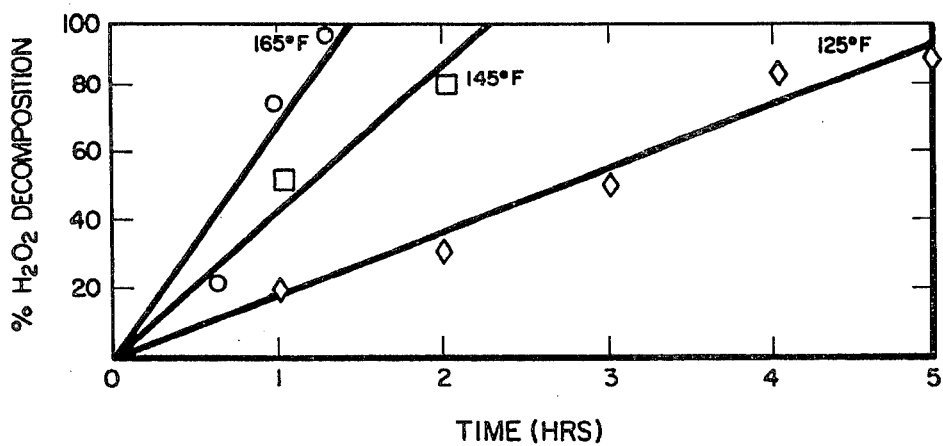
FIG. 4 is a graph showing the stability of the treatment solution as a function of temperature.

Alkaline solutions of hydrogen peroxide are inherently unstable and as is shown in FIG. 4, the stability of these solutions is very dependent upon temperature. The possibility of using the alkaline peroxide process at lower temperatures was evaluated and it was determined that for both Ti-6Al-6V-2Sn and Ti-6Al-4V titanium alloys, using a fifteen- to twenty-five-minute immersion time, a temperature range of from 165° F. (73.8° C.) to 125° F. (51.7° F.) is possible; 145° F. (62.7° C.) would be the preferred bath temperature and twenty minutes would be the preferred immersion time in order to obtain optimal bonding results. However, if it is desired to further reduce the usage of hydrogen peroxide, a lower temperature and a low immersion time should still produce acceptable results.

As the titanium is being etched in the alkaline peroxide pre-bond treatment solution, the concentration of the hydrogen peroxide is decreasing. An effort was therefore made to establish the lower concentration limit of hydrogen peroxide which could be used without sacrificing bond quality. Concentrations of hydrogen peroxide ranging from 0.001 molar to about 0.2 molar were added to 145° F. (62.7° C.) solutions of 0.5 molar NaOH to determine what, if any, effects these lower concentration ranges would have both on the initial strength and on the durability of bonded specimens. As can be seen from the data presented in Table II, the initial peel strength was not significantly dependent on hydrogen peroxide concentration. More importantly, the durability (the peel strength following exposure) of these specimens also remained unchanged and there was no evident bond degradation around the specimen edges. These results indicate that a wide concentration range of hydrogen peroxide of from about 0.001 molar to about 0.2 molar can be used without adversely affecting bonding properties. After making allowances for the difficulty of making accurate concentration measurements at the lower extremes of this experimentally verified range, and in view of the desirability of avoiding excessively high concentrations which will further increase the rate at which the peroxide must be replenished, it is presently preferred that the peroxide concentration be maintained at about 0.001 molar to about 0.01 molar or, if a wide range is desired, to about 0.1 molar.

TABLE II

| Peroxide Concentration (Molar) | −67° F. (−55° C.) Peel Initial | | −67° F. (−55° C.) Peel After 500 hrs at 150° (65.5° C.), 95% Relative Humidity | |
|---|---|---|---|---|
| | in-lbs/in | cm-kg/in | in-lbs/in | cm-kg/in |
| .047−.026 | 46 | 20.9 | 45 | 20.5 |
| .026−.0045 | 47 | 21.4 | 44 | 20.0 |
| .0086−.0045* | 47 | 21.4 | 43 | 19.5 |
| .023−.009* | 52 | 23.6 | 45 | 20.5 |
| .150−.001 | 42 | 19.0 | 43 | 19.5 |
| .022−.001* | 36 | 16.4 | 31 | 14.9 |

*Hydrogen Peroxide Added During Processing

The effect of varying the sodium hydroxide concentration on bond performance was also evaluated. Deviations in concentrations from the previously preferred value of 0.5 molar and ranging from 0.3 to 0.9 molar NaOH were added to 145° F. (62.7° C.) 0.2 molar hydrogen peroxide solutions. The results of the initial strength and the durability tests performed on these specimens appear unaffected by such deviation, although a few specimens exhibited some subjective differences with respect to roughness on the surface. Based on the above and on the fact that the peroxide is less stable in a more alkaline solution, the alkaline peroxide's sodium hydroxide constituent is preferably maintained at a concentration of about 0.3 to 0.5 molar.

Figure 5:
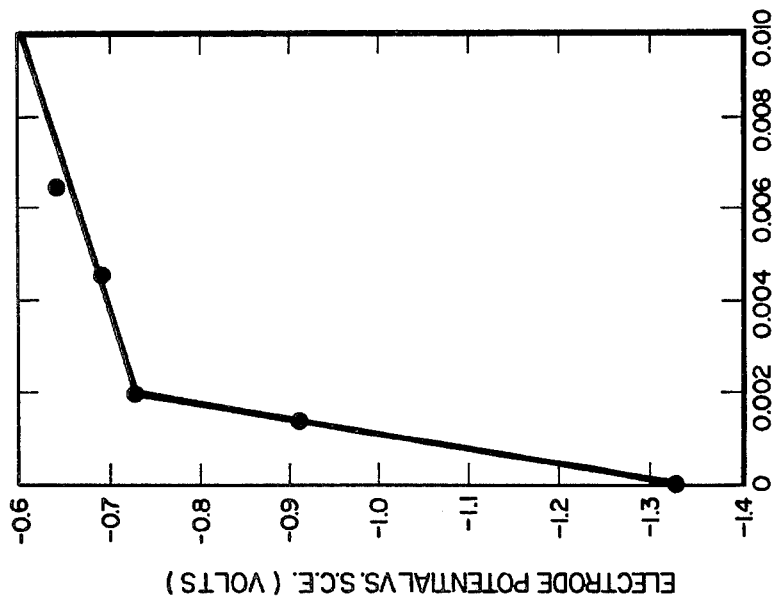
FIG. 5 is a graph showing the electrochemical potential between the magnesium electrode-saturated calomel electrode pair as a function of the solution's hydrogen peroxide concentration.

Attempts were made to monitor the aqueous treatment solution's peroxide concentrations by means of conventional inert electrodes such as platinum and carbon. However, such electrodes were found to adsorb certain contaminants from the solution and could not be used reliably. As an alternative to such chemically inert substances, an electrode material was sought which would ensure maintenance of a relatively uncontaminated electrode surface. It was found that pure magnesium metal provided such an electrode material, the surface of the magnesium electrode being slowly dissolved by the treatment bath so as to present a metallic surface with which is associated a stable potential characteristic that depends only on the concentration of the hydrogen peroxide. The typical electrochemical potential of a magnesium electrode (measured with respect to a saturated calomel electrode (S.C.E.)) is shown in FIG. 5. Notice that the magnesium electrode/S.C.E. response vs. peroxide concentration curve is relatively steep to about 0.002 molar concentration and then tends to level out beginning at about −0.7 Volts. This relationship is quite reproducible as long as there is some hydrogen peroxide present and the electrode is manually abraded to provide a fresh surface on an occasional (i.e., once per day) basis.

Such a magnesium electrode cannot be used reliably to detect peroxide concentrations less than about $10^{-4}$ molar because it demonstrates some tendency toward drift in this very low concentration range. However, this is not considered a significant disadvantage since it is intended that peroxide concentration be above this level. Furthermore, in that very low concentration range, the treatment solution generally tends to become rather turbid due to the formation of an insoluble titanium oxide species; the turbidity diminishes as the peroxide concentration is increased.

Figure 6:
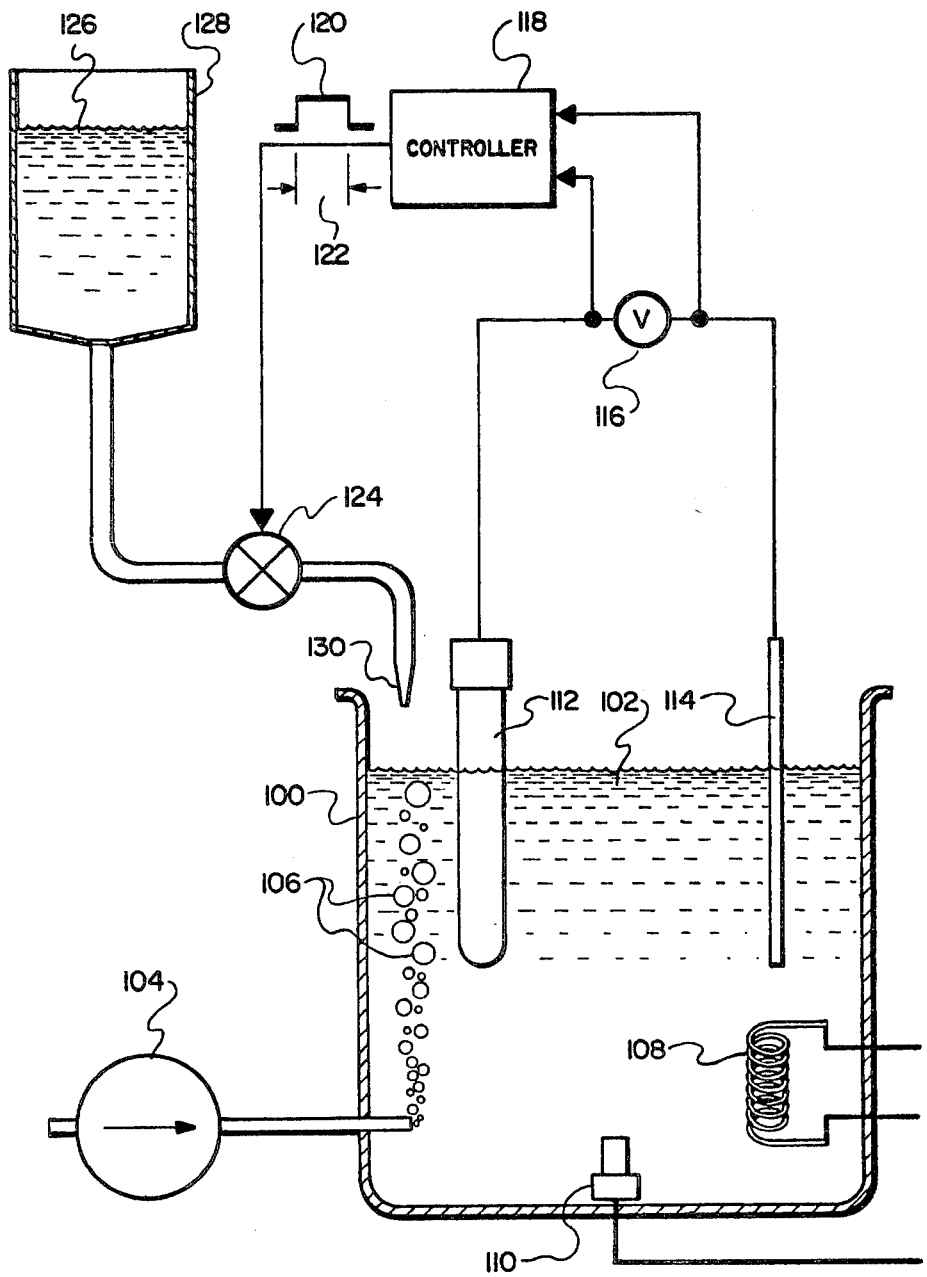
FIG. 6 is a conceptual diagram of an automated peroxide feed system.

A conceptual diagram of an automated peroxide feed system is shown in FIG. 6.

Referring specifically to that Figure, it may be seen that the treatment tank (100) is filled with the treatment solution (102). As noted above, the aqueous treatment solution preferably comprises an alkaline constituent such as sodium hydroxide or other strong base having a concentration of about 0.3 molar to about 0.5 molar; an oxidizing agent such as hydrogen peroxide; and a peroxide stabilizing substance such as magnesium silicate in the amount of approximately 0.5% by weight. Although the peroxide concentration may vary within relatively wide limits and therefore the initial concentration of the hydrogen peroxide is not critical, it may, for example, be from about 0.001 molar to about 0.01 molar. A source of compressed air (104) supplies air bubbles (106) which agitate the solution (102) and ensures that it is relatively homogeneous throughout the treatment tank (100) both with respect to chemical composition and with respect to physical properties such as temperature. A heater (108) is provided within the tank (100) and preferably is contained within inert Teflon coils so that the solution has no chemical effect on the heater elements or vice versa. A thermostat (110) is also provided which controls the heater (108) so as to maintain the treatment solution (102) at the required temperature. As discussed previously, the temperature will preferably be about 145° F. (62.7° C.) although for certain applications a lower temperature might be desirable. A pair of electrodes, namely, a saturated calomel reference electrode (112) and a pure metal magnesium electrode (114), are each partially immersed into the treatment solution (102) and are electrically connected to a volt meter (116), as well as to a control circuit (118) which monitors the voltage across the pair of electrodes (112, 114) and which, as the difference in voltage decreases to a predetermined lower threshold value (indicating that the lower limit of the preferred peroxide concentrations is about to be reached), generates a control pulse (120) having a predetermined duration (122) which causes a remote controlled valve (124) to be opened for a corresponding predetermined period of time, thereby allowing a predetermined quantity of concentrated hydrogen peroxide solution (126) contained in a hydrogen peroxide reservoir (128) to enter the treatment bath (100) via an inlet spout (130) whereupon it is mixed with the treatment solution (102) already contained in the bath (100) as a result of the agitation effects caused by the air bubbles (106), thereby raising the peroxide concentration of the treatment solution (102) to a value well above the above-mentioned lower limit. As discussed previously, a preferred concentration range for the hydrogen peroxide within the treatment solution (102) is from about 0.001 molar to about 0.01 molar. Accordingly, the controller (118) should be adjusted such that when the voltage difference between the S.C.E. electrode (112) and the Mg electrode (114) corresponds to a peroxide concentration of about 0.002 molar ($-0.8$ volts—see FIG. 5), then the valve (124) is opened for a duration (122) which permits a sufficiently large dose of concentrated hydrogen peroxide to be added to the solution (102) to cause the solution's hydrogen peroxide concentration to revert close to its upper limit, for example, aboout 0.01 molar. It should be appreciated that these values are approximate and in view of the relative insensitivity to hydrogen peroxide concentration in the above-described treatment process, there is no particular necessity to provide a control circuit (118) that is especially sensitive or accurate or which is capable of controlling the instantaneous rate of flow from the reservoir (128) to the tank (100).

Figure 8B:
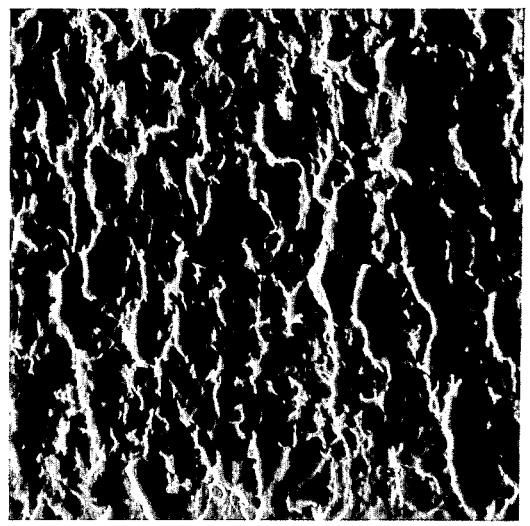
FIGS. 8a and 8b are a pair of photomicrographs comparing the titanium surface morphology resulting from alkaline peroxide treatment solutions respectively not containing and containing a stabilizing inhibitor.
Figure 8A:
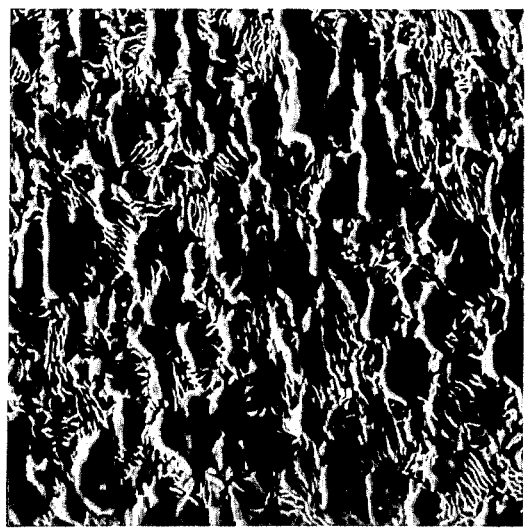

Substances which contain chemical entities such as phosphates, pyrophosphates, silicates and magnesium ion tend to inhibit the decomposition of alkaline peroxide solutions. The ability of these and other substances to retard peroxide decomposition without affecting bond properties was investigated. Candidate inhibitors were introduced into 145° F. (62.7° C.) solutions containing 0.5 molar NaOH and 0.2 molar initial hydrogen peroxide concentrations. The concentration of peroxide was monitored at various time increments by means of a conventional wet chemical method. The result of these studies are given graphically in FIG. 7. Notice that sodium perborate, sodium citrate and sodium pyrophosphate alone provided no significant improvement in decomposition rate over the untreated solution, whereas mixtures of inhibitors which included both sodium silicate and magnesium sulfate were effective in retarding peroxide decomposition. Such magnesium salt and silicate mixtures resulted in the formation of a magnesium silicate gel which apparently was capable of absorbing the catalytic cationic species. In order to determine if a magnesium silicate inhibitor had any adverse effects on the adherend surface, durability and peel specimens were prepared in a 145° F. (62.7° C.) solution containing 0.5 molar NaOH and 0.5 wt % $MgSiO_3$ with an initial peroxide concentration of about 0.2 molar. The specimens were bonded onto a primed 2024-T3 aluminum plate and tested. Representative $-67°$ F. ($-55°$ C.) peel test data from these specimens are provided in Table III. The final specimen indicated in Table III was prepared about 8 hours after the first. Notice that more than half the original peroxide still remained at the end of the test period. This can be compared to untreated solutions in which the vast majority of the peroxide dissipates within 2 to 4 hours depending on solution contamination levels. While there was no apparent decrease in either the initial strength or durability properties of these specimens when compared with those prepared using the unstabilized solution, the stabilized solution did not appear to create quite the same degree of surface roughness as the unstabilized solution as can be seen in the photomicrographs shown in FIGS. 8a and 8b. With respect to durability, it should be noted that there was no visible disbond penetration following prolonged exposure to high humidity in any of the test specimens treated with an alkaline peroxide solution containing the $MgSiO_3$ stabilizing inhibitor.

TABLE III

| Peel Test Data for Ti-6Al-6V-2Sn Specimens Prepared in Alkaline Peroxide Solutions Containing 0.5% $MgSiO_3$ Inhibitor by Weight | | |
|---|---|---|
| $H_2O_2$ Molarity | $-67°$ F. ($-55°$ C.) Peel | |
| | (in-lbs/in) | (cm-kg/cm) |
| .152 | 49 | 22.3 |
| .151 | 48 | 21.8 |
| .144 | 46 | 20.9 |
| .142 | 48 | 21.8 |
| .133 | 46 | 20.9 |
| .139 | 43 | 19.5 |
| .106 | 44 | 20.0 |
| .133 | 44 | 20.0 |
| .124 | 44 | 20.0 |
| .119 | 45 | 20.5 |
| .119 | 45 | 20.5 |
| .112 | 42 | 19.1 |
| .113 | 46 | 20.9 |
| .107 | 42 | 19.1 |
| .097 | 51 | 23.2 |
| .096 | 54 | 24.5 |
| .088 | 58 | 26.4 |

It is apparent that there has been provided with this invention a novel Improved Pre-Bond Surface Treatment of Titanium which fully satisfies the objects, means and advantages as set forth hereinbefore. While the invention has been described in combination with specific embodiments thereof, it is evident that many alternatives, modifications and variations will be apparent to those skilled in the art in light of the foregoing description. Accordingly, it is intended to embrace all such alternatives, modificationa and variations as fall within the spirit and broad scope of the appended claims.

We Claim:

1. An automated system for maintaining the concentration of hydrogen peroxide within an alkaline peroxide treatment solution at a value in excess of a predetermined lower limit, said system comprising:

a treatment tank;

a treatment solution contained within said treatment tank;

means for agitating said solution within said treatment tank so as to ensure that said solution is relatively homogeneous both with respect to chemical composition and with respect to physical properties;

a first electrode;

a second electrode consisting essentially of pure magnesium metal, said first and second electrodes both being at least partially immersed into said treatment solution within said treatment tank;

a reservoir containing concentrated hydrogen peroxide solution;

a remotely controllable valve operatively interposed between said reservoir and said treatment tank so as to control the flow of said concentrated hydrogen peroxide solution from said reservoir to said tank; and circuit means for monitoring the voltage across said first and second electrodes and for generating a control pulse to open said valve as said voltage decreases to a predetermined lower threshold voltage.

2. The automated system of claim 1, wherein said first electrode is a saturated calomel electrode.

3. The automated system of claim 1, wherein said lower threshold voltage corresponds to a hydrogen peroxide concentration of less than approximately 0.002 molar.

* * * * *

UNITED STATES PATENT AND TRADEMARK OFFICE
CERTIFICATE OF CORRECTION

PATENT NO. : 4,477,329

DATED : October 16, 1984

INVENTOR(S) : ALISA K. ROGERS, et al.

It is certified that error appears in the above-identified patent and that said Letters Patent is hereby corrected as shown below:

On the title page, inventors should read:

-- Inventors: Alisa K. Rogers, Granada Hills;
Kenneth E. Weber, Pracific Palisades,
Steven D. Hoffer, San Jose,
all of Calif.

*Signed and Sealed this*

*Second* Day of *July 1985*

[SEAL]

*Attest:*

DONALD J. QUIGG

*Attesting Officer*     *Acting Commissioner of Patents and Trademarks*